(12) United States Patent
Jono et al.

(10) Patent No.: US 8,942,523 B2
(45) Date of Patent: Jan. 27, 2015

(54) PROBE

(75) Inventors: Junichi Jono, Kita-ku (JP); Toshinori Takimura, Hachioji (JP); Shoichi Tao, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 13/881,928

(22) PCT Filed: Oct. 20, 2011

(86) PCT No.: PCT/JP2011/074184
§ 371 (c)(1),
(2), (4) Date: Apr. 26, 2013

(87) PCT Pub. No.: WO2012/056991
PCT Pub. Date: May 3, 2012

(65) Prior Publication Data
US 2013/0209034 A1    Aug. 15, 2013

(30) Foreign Application Priority Data

Oct. 26, 2010  (JP) .................................. 2010-239447

(51) Int. Cl.
| G02B 6/32 | (2006.01) |
| G01N 21/01 | (2006.01) |
| A61B 5/00 | (2006.01) |
| G01N 21/64 | (2006.01) |

(52) U.S. Cl.
CPC .............. G01N 21/01 (2013.01); A61B 5/0071 (2013.01); A61B 5/0084 (2013.01); G01N 21/645 (2013.01); *G01N 2021/6484* (2013.01)
USPC ................ 385/33; 385/34; 385/117; 385/119

(58) Field of Classification Search
CPC ............... A61B 5/0084; G01N 21/645; G01N 2021/6484
USPC ....................................... 385/31–34, 117–121
See application file for complete search history.

(56) References Cited

U.S. PATENT DOCUMENTS

| 7,235,047 B2 * | 6/2007 | MacAulay et al. ............ 600/182 |
| 7,347,631 B2 * | 3/2008 | Suzuki et al. .................... 385/88 |

FOREIGN PATENT DOCUMENTS

| JP | 1-244416 | 9/1989 |
| JP | 3-107751 | 5/1991 |
| JP | 11-281582 | 10/1999 |
| JP | 2010-88665 | 4/2010 |
| JP | 2010-088929 | 4/2010 |
| JP | 2010-104391 | 5/2010 |
| JP | 2010-158358 | 7/2010 |

* cited by examiner

*Primary Examiner* — Ellen Kim
(74) *Attorney, Agent, or Firm* — Cozen O'Connor

(57) ABSTRACT

Optical probe having, independently, an irradiation light guide path for irradiation light and a received light guide path for acquiring radiated light. A first optical fiber configures the irradiation light guide path, and a second optical fiber configures the received light guide path. A condensing lens receives on one surface irradiation light from the first optical fiber and emits same on the other surface, and receives radiated light radiated from the other surface and concentrates same on the side of the first and second optical fibers. The central axis of the exit end of the first optical fiber is deviated relative to the optical axis of the condensing lens, moving reflected light at the condensing lens surface away from, and moving radiated light concentrated by the condensing lens closer to, the center of the light-receiving end of the second optical fiber.

11 Claims, 8 Drawing Sheets

PROBE

RELATED APPLICATIONS

This is a U.S. national stage of International application No. PCT/JP2011/074184 filed on Oct. 20, 2011.

This patent application claims the priority of Japanese application no. 2010-239447 filed Oct. 26, 2010, the disclosure content of which is hereby incorporated by reference.

TECHNICAL FIELD

The present invention relates to a probe having an optical system which illuminates an illumination light to a site of measurement of a biological tissue and receives a radiative light radiated from the site of measurement, directed to measurement of the radiative light.

BACKGROUND ART

Observation or diagnosis of internal hollow organ using an electronic endoscope is a widely disseminated method of diagnosis at present. By virtue of its direct feature of observation, the method is ready to discriminate normal tissue and lesioned part, and for which continuous efforts have been directed to improve quality of captured image.

On the other hand, besides so-called videoscope, diagnostic equipments based on various optical principles and ultrasonic diagnostic equipments have been proposed, and a part of which have been put into practical use.

In particular, there has been proposed a fluorescence imaging endoscope system which uses fluorescent light to acquire information invisible to naked eyes to configure an fluorescent image, and displays it so as to be overlapped with a visible image (for example, Patent Document 1). This sort of system will be useful for early detection of malignant tumor, and is counted on greatly.

Another known method, although without configuring the fluorescent image, is such as acquiring intensity information of fluorescence, so as to determine the status of tissue (for example, Patent Document 2). Most of this type of methods are configured to acquire fluorescence without using an image sensor mounted on the electronic endoscope.

Known types of a diagnosing element for enabling the fluorescent diagnosis, or "probe", include those guided into body through a forceps channel of the endoscope, and those integrated with the endoscope (note that the forceps channel means a tunnel-like path allowing a treatment tool such as forceps or catching net to pass therethrough, also referred to as a working channel, insertion channel or the like.). The probes for fluorescence observation described in Patent Documents 1 and 2 are to be inserted into body while being inserted through the forceps channel of the endoscope.

For inspection inside human body, the probe is sometimes required to be simplified in the structure thereof, in view of thinning the probe for reducing physical burden on patients and making the probe disposable aiming at preventing infection or facilitating the inspection. While the configuration of the probe may possibly be simplified by making the fiber available both for illumination and receiving, or omitting the light receiving fiber, it is indispensable for accurate measurement to use a illumination light guide for guiding therethrough an excitation light, and a receiving light guide for acquiring fluorescence, for either types, even for the case where the probe is used independently from the endoscope. As a configuration having both of illumination fiber and light receiving fiber, Patent Document 3 describes an endoscope system having a center fiber for guiding the illumination light, and a plurality of light receiving fibers arranged therearound.

PRIOR ART DOCUMENTS

Patent Documents

PATENT Document 1: Japanese Patent Application Laid Open Publication No. 2010-104391
PATENT Document 2: Japanese Patent Application Laid Open Publication No. 2010-88929
PATENT Document 3: Japanese Patent Application Laid Open Publication No. 2010-158358

DISCLOSURE OF THE INVENTION

Problems to be Solved by the Invention

The prior arts have, however, been suffering from the problems below.

The probe for fluorescence observation described in Patent Document 1 has the illumination light guide for guiding the excitation light but has no receiving light guide for acquiring fluorescence therethrough, wherein fluorescence is received by CCDs of the endoscope to thereby acquire a fluorescent image. Accordingly, a fluorescence observation function cannot be completed by the probe alone, and this makes it difficult to ensure accurate measurement.

The probe for fluorescence observation described in Patent Document 2 uses the single optical fiber for guiding both of the excitation light and fluorescence, and separates the excitation light and fluorescence using a dichroic mirror disposed on a base unit. In this configuration using the single optical path for the both, loss of luminous energy of fluorescence, having been guided to the base unit, is inevitable, and this degrades detectability of lesion. Increase in the luminous energy of excitation light to be illuminated may adversely affect human body. Decrease in the luminous energy may make the accurate measurement difficult.

The endoscope system described in Patent Document 3 has the illumination fiber and light receiving fibers independent from each other, but has no optical element such as condensing lens. Therefore, the illumination optical fiber has to be entirely surrounded by a large number of light receiving fibers to surely receive the light, and this makes the system disadvantageous in terms of further reduction in diameter and further simplification of the structure.

The present invention is conceived after considering the above-described problems in the prior arts, and an object of which is to provide a probe having an optical system which illuminates an illumination light to a site of measurement of a biological tissue and receives a radiative light radiated from the site of measurement, and configured so as to measure the radiative light, wherein the probe is such as having an illumination light guide for illuminating an illumination light and a receiving light guide for acquiring the radiative light, which are independent from each other, making the probe simple in the configuration and highly efficient to acquire the radiative light to be measured.

Means for Solving the Problem

The invention described in claim 1 to solve the above problems is a probe having an optical system which illuminates an illumination light to a site of measurement of a biological tissue and receives a radiative light radiated from the site of measurement, and configured so as to measure the radiative light, wherein the prove includes a first optical fiber which configures an illumination light guide through which the illumination light is guided and a second optical fiber which configures a receiving light guide through which the radiative light is acquired, the first optical fiber and the second optical fiber being independent from each other, and a condensing lens which receives the illumination light output from the first optical fiber and outputs the received illumination light towards the site of measurement and which receives the radiative light radiated from the site of measurement and condenses the received radiative light towards the optical fiber, and the first optical fiber being aligned so as to shift the center axis of the output end of the first optical fiber away from the optical axis of the condensing lens or/and relatively inclined from the optical axis of the condensing lens, and when compared with a configuration without the shift and the inclination, a reflected light from a surface of the condensing lens being brought away from the center of the input end of the second optical fiber and the radiative light condensed by the condensing lens being brought closer to the center of the input end of the second optical fiber.

The invention described in claim 2 is the probe of claim 1 wherein, in a plane normal to the optical axis of the condensing lens, a center of distribution of the reflected light from the condensing lens is positioned opposite to the center of the output end of the first optical fiber while placing the optical axis of the condensing lens in between, and the center of condensation of the radiative light is positioned closer to the center of the output end of the first optical fiber, than to the optical axis of the condensing lens.

The invention described in claim 3 is the probe of claim 1 or 2 wherein the center axis of the output end of the first optical fiber is relatively shifted from the optical axis of the condensing lens, and the center axis of the input end of the second optical fiber is positioned closer to the optical axis of the condensing lens than to the center axis of the output end of the first optical fiber.

The invention described in claim 4 is the probe of claim 3 wherein the center axis of the input end of the second optical fiber is positioned between the center axis of the output end of the first optical fiber and the optical axis of the condensing lens.

The invention described in claim 5 is the probe of any one of claims 1 to 4 wherein the numerical aperture of the second optical fiber is larger than the numerical aperture of the first optical fiber.

The invention described in claim 6 is the probe of any one of claims 1 to 4 comprising one or a plurality of the first optical fibers and one or a plurality of the second optical fibers, wherein the total core area of the second optical fiber(s) is larger than the total core area of the first optical fiber(s).

The invention described in claim 7 is the probe of any one of claims 1 to 6 including a plurality of the second optical fibers, wherein the input ends of the plurality of second optical fibers are arranged to be gathered at the center of condensation of the radiative light condensed by the condensing lens.

The invention described in claim 8 is the probe of claim 7, wherein an average distance from the input ends of the plurality of second optical fibers to the optical axis of the condensing lens is shorter than an average distance from the input ends of the plurality of second optical fibers to the center of the output end of the first optical fiber.

The invention described in claim 9 is the probe of any one of claims 1 to 8 wherein the illumination light or the radiative light has a wavelength of 300 nm to 1100 nm.

The invention described in claim 10 is the probe of any one of claims 1 to 8 wherein the illumination light or the radiative light has a wavelength of 340 nm to 750 nm.

The invention described in claim 11 is the probe of any one of claims 1 to 10 wherein the distance between the center axis of the first optical fiber and the center axis of the second optical fiber is shorter than a diameter of the second optical fiber.

Advantageous Effects of Invention

According to the present invention, the illumination light to be illuminated onto a site of measurement of a biological tissue is guided through the first optical fiber, and the radiative light radiated from the site of measurement is received and guided in an efficient manner by the second optical fiber, provided separately from the first optical fiber, so that the radiative light to be measured may be acquired in a successful manner.

EMBODIMENTS FOR CARRYING OUT THE INVENTION

An embodiment of the present invention will be described referring to the attached drawings. The description below deals with one embodiment of the present invention, without limiting the present invention. The embodiment below will be described referring to a probe for fluorescence observation.

A probe 10 of this embodiment includes a first optical fiber 1, a second optical fiber 2, and a condensing lens 3.

The end portion of the first optical fiber 1, the end portion of the second optical fiber 2, and the condensing lens 3 are kept in a fixed positional relation by a frame component (not illustrated) having a given form.

The outer circumference of the probe 10 is configured by a flexible tube. The probe 10 has, on the end face thereof, a window for outputting and receiving light, which is water-tightened so as to avoid infiltration of liquid therein.

The base end of the probe 10 is connected to a base unit which is not illustrated. A light source of excitation light, a spectrometer, an analyzer and so forth are configured on the base unit. The base end of the first optical fiber 1 is connected to the light source, and the base end of the second optical fiber 2 is connected to the spectrometer.

Figure 1:
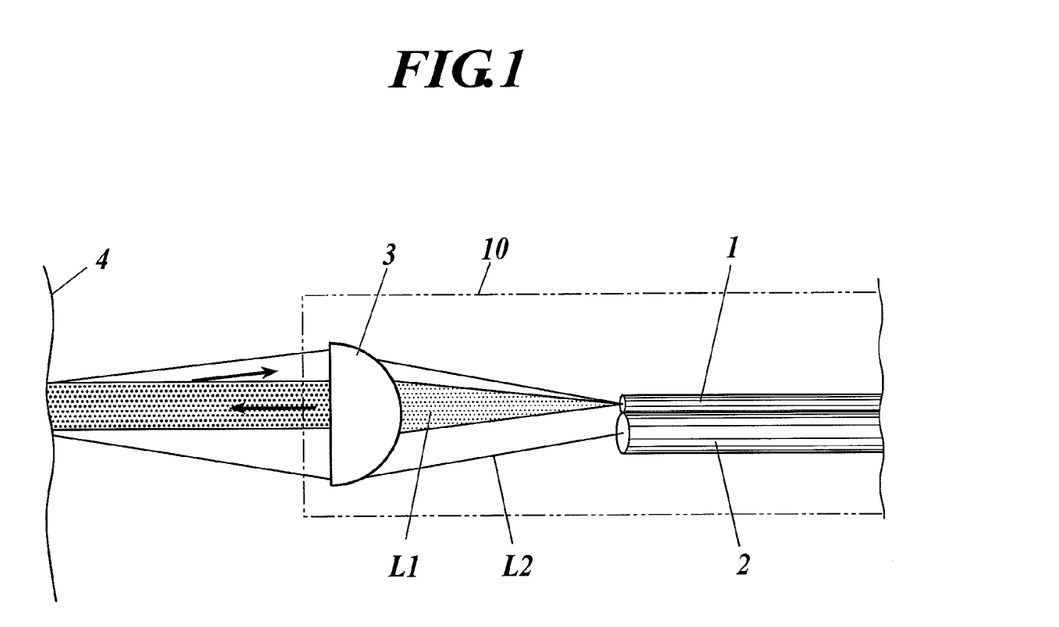
FIG. 1 This is a schematic side elevation illustrating an arrangement at the end of a probe according to one embodiment of the present invention.

As illustrated in FIG. 1, an excitation light L1 output from the first optical fiber 1 is condensed by the condensing lens 3 and output from the probe 10, and is illuminated on a site of measurement on the surface of a biological tissue 4. Upon being illuminated by the excitation light L1, fluorescence generates at the site of observation depending on the status of lesion. Radiative light L2 from the site of measurement, which contains the generated fluorescence and the reflected light from the surface of the biological tissue 4, enters the probe 10, condensed by the condensing lens 3, and then enters the second optical fiber 2.

Light guided through the second optical fiber 2 is input to the spectrometer of the base unit. Fluorescence in a broad sense is an excessive energy emitted in the form of electromagnetic wave, when electrons in an object, irradiated by X-ray, ultraviolet radiation or visible light, absorb the energy to be excited, and then fall down to the ground state. With the aid of the excitation light (reference light), the fluorescence is generated as an optical feedback with a wavelength different from that of the excitation light. The status of lesion of the object to be detected may be known by detecting the optical feedback, by guiding it through the second optical fiber 2 to the spectrometer of the base unit for spectral distribution analysis.

Mode of insertion of the probe 10 into the body may be such as insertion through a channel formed in the endoscope, or may be insertion alone by itself, independent of the endoscope.

A way of propagation of the excitation light concentrated on a living body is variable by selecting a relative distance between the condensing lens 3 and the first optical fiber 1. By arranging the condensing lens 3 and the first optical fiber 1 so as to collimate the excitation light to thereby allow illumination in parallel with the optical axis, a stable measurement is ensured since the spot geometry of excitation light L1 illuminated on the living body will not vary even if the position of the surface of the biological tissue moves back and forth along the optical axis.

A mode of ensuring condensation of the excitation light onto a single point on the surface of the biological tissue is also advantageous for highly sensitive measurement, since a recovery efficiency of the optical feedback from the living body will be improved.

For the probe configured so as to be insertable into the channel formed in the endoscope, the outer diameter thereof, insertable for example into a 9F channel (corresponded to 3 mm in diameter), is approximately 2.8 (mm) or thinner, and optical components incorporated therein have to be further smaller. In one Example, the radius of curvature of the lens 3 is set to 0.68 mm to 0.83 mm, and two optical fibers each having a core diameter of about 0.1 to 0.5 mm, generally called multi-mode fiber, are used as the first optical fiber 1 and the second optical fiber 2.

[Core Diameter]

By selecting the core diameter of the second optical fiber 2 equal to or larger than the core diameter of the first optical fiber 1, it is now possible by the spectral detection to detect the light emission contained in the radiative light L2 in a highly efficient manner.

Since the radiative light L2 has a directionality smaller than that of the excitation light L1, the radiative light L2 condensed by the lens 3 is generally spread wider than the core diameter of the first optical fiber 1. Accordingly, in this type of system, a larger quantity of luminous energy of radiative light L2 may be introduced into the second optical fiber 2, by selecting the core diameter of the second optical fiber 2 larger than that of the first optical fiber 1.

Alternatively, a similar effect may be obtained by increasing the number of the second optical fibers 2, in place of increasing the core diameter of the second optical fiber 2. More specifically, by providing one or a plurality of the second optical fibers 2 with the total core area of the second optical fibers 2 larger than that of the first optical fiber 1, the radiative light L2 from the living body may be acquired in a highly efficient manner.

The lower limit of the core diameter of the second optical fiber 2 is equal to the core diameter of the first optical fiber 1. Improvement in the light reception efficiency, through increase in the core diameter of the second optical fiber 2, may be achieved within the range of the core diameter of optical fibers which are generally available, wherein the upper limit value of the core diameter thereof may be set to 1 (mm).

Note, however, that the upper limit value of the core diameter of the second optical fiber 2 is limited by an effective diameter of the lens 3. This is because the entire cores of the first and second optical fibers 1, 2 have to fall within the range of the effective diameter of the lens 3 when viewed along the optical axis of the lens. Accordingly, the core diameter of the second optical fiber 2 may be set not larger than the effective radius of the lens 3. This will further be explained referring to Referential Calculation Example 1.

Referential Calculation Example 1

Core Diameter and Received Light Power

Figure 2:
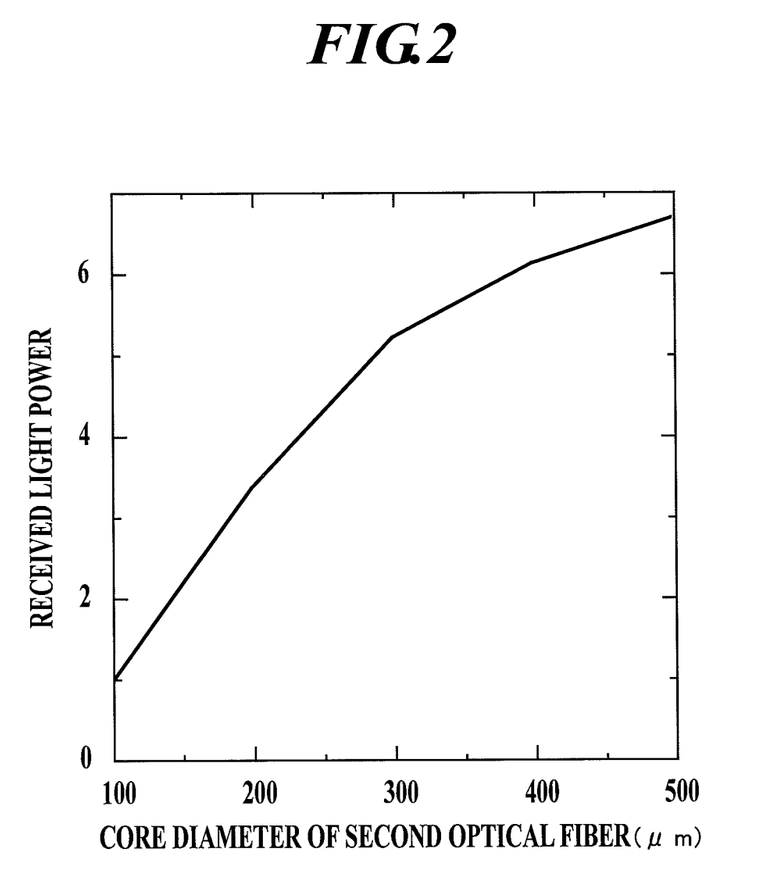
FIG. 2 This is a graph illustrating a relation between the core diameter of a second optical fiber and relative power of received light, in a probe according to one example of the present invention, wherein the relative power of received light for a core diameter of the optical fiber of 100 μm is assumed as 1.

FIG. 2 is a graph illustrating a relation between the core diameter of the second optical fiber 2 and received light power calculated based on the conditions below.

(Conditions for Calculation)

Conditions for the first optical fiber include a core diameter of 105 (μm), a NA of 0.23 and a shift from the optical axis of lens of 0 (mm).

Conditions for the second optical fiber include the core diameter varies among 100 (μm), 200 (μm), 300 (μm), 400 (μm) and 500 (μm), a clad diameter of 1.1 times as large as the core diameter and a NA of 0.22.

The lens is a semi-spherical lens, with a radius of curvature of the surface opposed to the optical fiber of 0.68 (mm), an effective diameter of 1.36 (mm), a lens thickness of 0.68 (mm) and a radius of curvature of the surface opposite to the optical fiber of infinity (i.e., flat surface). The lens is also characterized by $n_d$=1.5163 and $v_d$=64.1.

The distance between the optical fiber and the surface of the lens opposed thereto is 1.125 (mm), the distance between the optical fiber and a sample to be measured is 3.505 (mm) and the first optical fiber and the second optical fiber are arranged so as to be brought into contact with each other with the outer circumferential surfaces thereof.

As seen in the graph in FIG. 2, the received light power increases as the core diameter increases.

It is, however, confirmed that rate of increase of the received light power gradually decreases as the core diameter increases, showing a considerably lowered rate of increase in the received light power at around a core diameter of 0.5 mm, under an effective radius of 0.68 mm. There is no longer enough room for increase in the received light power even if the core diameter increases any more. The core diameter exceeding the effective radius of the lens 3 has almost no effect of increasing the received light power, and may be disadvantageous in terms of thinning. The core diameter of the second optical fiber 2 is, therefore, preferably not larger than the effective radius of the lens 3 as described above. For the case where a plurality of second optical fibers are used, it is not necessary that the lower limit value of the core diameter of every second optical fiber is in agreement with the core diameter of the first optical fiber, but it suffices that light is transmitted effectively and that the total core area is not smaller than the core area of the first optical fiber (for the case where a plurality of first optical fibers are used, the total core area of them).

[NA]

Alternatively, the light reception efficiency of the radiative light L2 may be increased by increasing NA of the second optical fiber 2 over NA of the first optical fiber 1. In this case, NA of both optical fibers 1, 2 is required to be smaller than a value of the right side of the formula 1 below, which is determined by distance f between the lens 3 and the optical fibers 1, 2 and effective diameter φ of the lens 3. This is because there is no need of emitting nor receiving light which does not pass through the lens 3.

That is, the formula 1 below has to be satisfied.

$$NA \leq \phi/\sqrt{(4f^2+\phi^2)} \quad \text{(formula 1)}$$

where, f represents focal length of lens, and φ represents effective diameter of lens.

Since the radiative light L2 propagate in random directions, the beam diameter of emission on the lens surface is generally larger than the beam diameter of the excitation light L1. For this reason, in order to receive a larger energy of radiative light L2, it is preferable to reduce NA of the first optical fiber 1 so as to allow larger energy of radiative light L2 to reach the lens 3 and to increase NA of the second optical fiber 2 so as to receive the radiative light L2 from a larger area of the lens surface.

The lower limit of NA of the second optical fiber 2 is equal to NA of the first optical fiber 1. Improvement in the light reception efficiency through increase in NA of the second optical fiber 2 may be achieved within the range of NA of optical fibers which are generally available, wherein the upper limit value thereof may be set to 0.48. Note, however, that the upper limit value of NA of the second optical fiber is determined by the formula 1 above, so far as the lens 3 is employed. This will be further detailed below referring to Referential Calculation Example 2.

Referential Calculation Example 2

NA and Received Light Power

Figure 3:
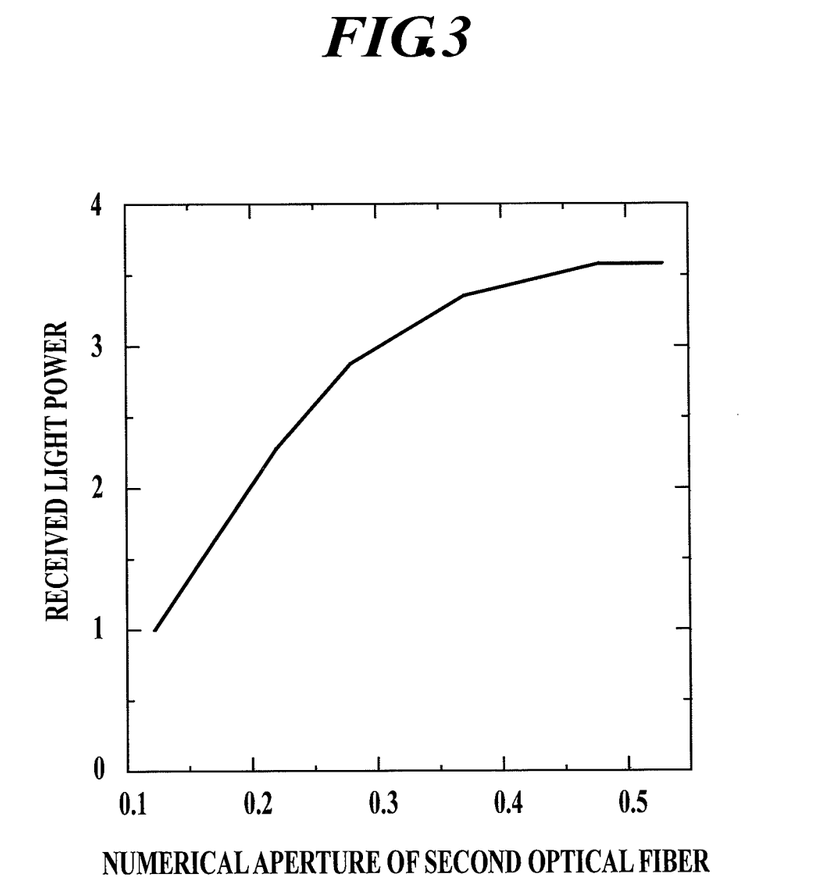
FIG. 3 This is a graph illustrating a relation between the numerical aperture (NA) of the second optical fiber and relative power of received light, in a probe according to one example of the present invention, wherein the relative power of received light for an NA of the optical fiber of 0.12 is assumed as 1.

FIG. 3 is a graph illustrating a relation between NA of the second optical fiber 2 and received light power, calculated according to the conditions below.

(Conditions for Calculation)

For the first optical fiber and the lens, conditions same as those described in Referential Calculation Example 1 are employed.

Conditions for the second optical fiber include a core diameter of 200 (μm), a clad diameter of 1.1 times as large as the core diameter and NA varying over the range from 0.12 to 0.53.

The distance between the optical fiber and the surface of the lens opposed thereto and the distance between the optical fiber and a sample to be measured are same as those in Referential Calculation Example 1, and the first optical fiber and the second optical fiber are again arranged so as to be brought into contact with each other with the outer circumferential surfaces thereof.

Substituting the above described conditions for the formula 1, now given is, $$\phi/\sqrt{(4f^2+\phi^2)}=1.36/\sqrt{(4*1.125^2+1.36^2)}=0.517 \approx 0.52.$$

As seen in the graph in FIG. 3, the received light power increases as NA increases.

However, while the upper limit value of NA determined from the equation 1 above is 0.52, results of calculation obtained herein shows that the light reception efficiency became almost constant at around a NA of the second optical fiber 2 of 0.5, indicating that increase in NA of the second optical fiber came to the limit of increase in the light reception efficiency.

Accordingly, in the configuration using the lens 3 as described above, the upper limit of NA of the second optical fiber 2 is given by the formula 1.

[Axial Offset Arrangement]

Referential Calculation Example 3

Arrangement of First Optical Fiber 1 and Distribution of Condensed Light

First, a referential calculation example will be shown.

Figure 4A:
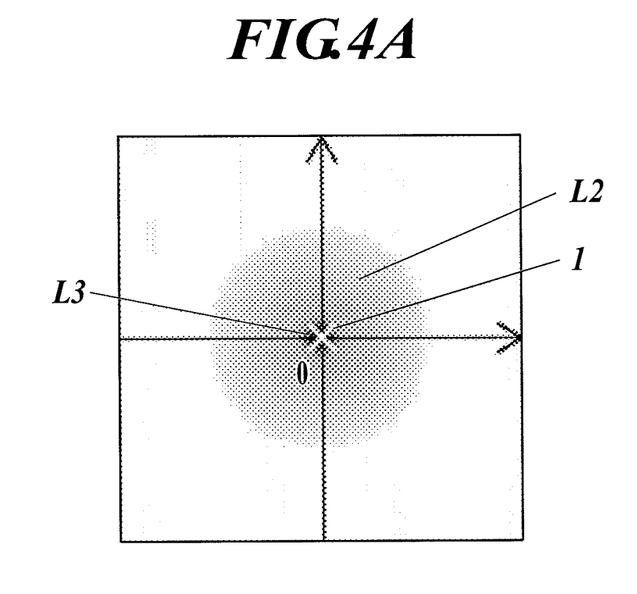
FIG. 4A This is a drawing illustrating a distribution of light in relation to the optical axis of a lens and the first optical fiber in a probe according to one example of the present invention, with the first optical fiber aligned on the optical axis of a lens 3.
Figure 4B:
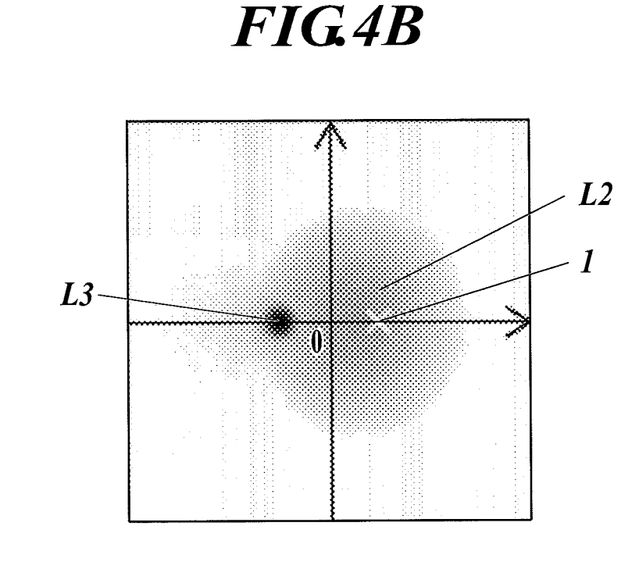
FIG. 4B This is a drawing illustrating a distribution of light in relation to the optical axis of the lens and the first optical fiber in the probe according to one example of the present invention, with the first optical fiber shifted 0.2 (mm) away from the optical axis of the lens 3.
Figure 4C:
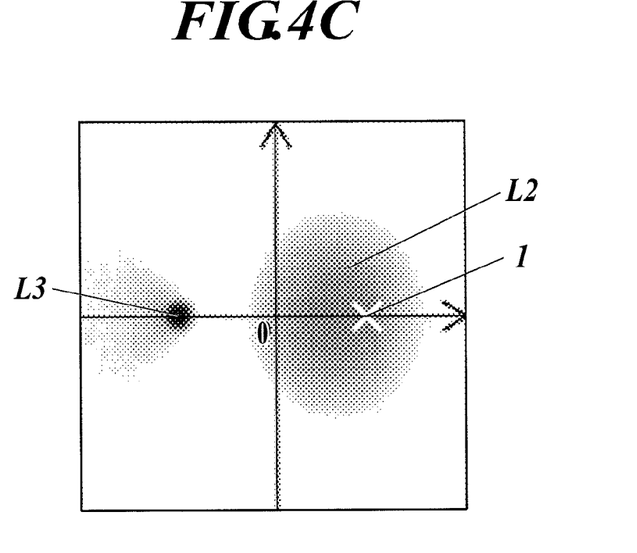
FIG. 4C This is a drawing illustrating a distribution of light in relation to the optical axis of the lens and the first optical fiber in the probe according to one example of the present invention, with the first optical fiber shifted 0.4 (mm) away from the optical axis of the lens 3.

FIG. 4A, FIG. 4B and FIG. 4C are two-dimensional distribution charts illustrating changes in distribution of the radiative light L2 and the reflected light L3 from the lens 3, corresponding to changes in the arrangement of the first optical fiber 1 on a plane coordinate normal to the optical axis. Marks "x" in the drawings indicate the center position of the first optical fiber 1. Each plane coordinate has the origin placed on the optical axis of the lens 3, laid on a plane which is normal to the optical axis, and contains the output end surface of the first optical fiber 1. Conditions for calculation are as follow. A range of distribution of the condensed radiative light L2 in the plane coordinate faintly spreads as seen in the drawing, whereas a range of distribution of the reflected light L3 from the lens 3 is densely pin-pointed within a narrow range.

(Conditions for Calculation)

Conditions for the first optical fiber include a core diameter of 100 (μm), a NA of 0.23 and the shift from the optical axis of the lens varying among (a) 0, (b) 0.2 and (c) 0.4 (mm).

The lens is a semi-spherical lens, with a radius of curvature of the surface opposed to the optical fiber of 0.83 (mm), an effective diameter of 1.66 (mm), a lens thickness of 0.83 (mm) and a radius of curvature of the surface opposite to the optical fiber of infinity (i.e., flat surface). The lens is also characterized by $n_d=1.51633$ and $v_d=64.1$.

The distance between the first optical fiber and the surface of the lens opposed thereto is 1.37 (mm) and the distance between the optical fiber and a sample to be measured is 3.9 (mm). Angular characteristic of the radiative light L2 is modeled as Lambertian reflectance.

As seen in FIG. 4A, when the first optical fiber 1 is aligned on the optical axis of the lens 3, the radiative light L2 is concentrated on the optical axis. Since the first optical fiber 1 in this case is aligned on the optical axis of the lens 3, the second optical fiber 2 is no longer aligned on the optical axis of the lens 3, and therefore a deviation generates between the center position of the second optical fiber 2 and the center of condensation of the radiative light L2. Accordingly, a configuration having the first optical fiber 1 aligned on the optical axis of the lens 3 suffers from a problem that the light reception efficiency of the radiative light L2 is not so high.

In contrast, by shifting the first optical fiber 1 away from the optical axis of the lens 3, as seen in FIG. 4B and FIG. 4C, it is now possible to make the center position of condensation of the radiative light L2 and the center position of the first optical fiber 1 be different, and thereby spatially separate the center position of condensation of the radiative light L2 and the center position of the first optical fiber 1 in a substantial manner. Accordingly, the second optical fiber 2 may be disposed at a position where density of condensation of the radiative light L2 is large, and thereby the light reception efficiency of the radiative light L2 by the second optical fiber 2 may be increased.

Figure 5:
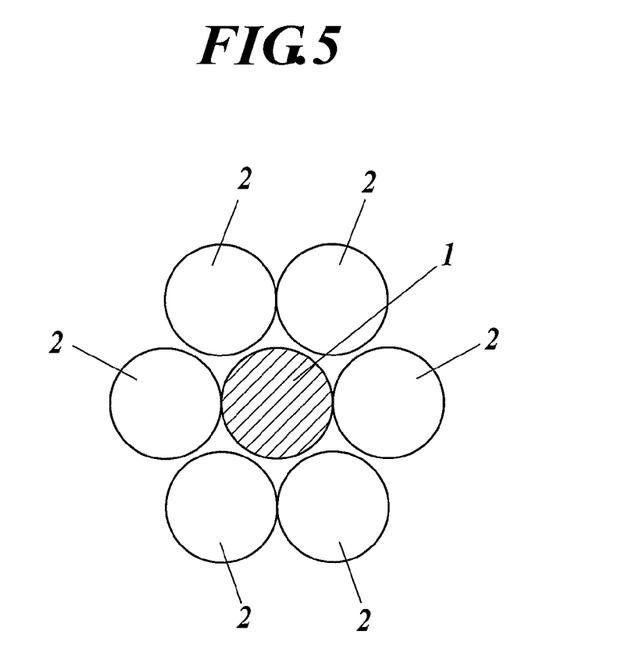
FIG. 5 This is a schematic front elevation illustrating an arrangement of optical fibers of a probe according to Comparative Example.

Assuming now the direction of shifting of the first optical fiber 1 as the X-direction, it is confirmed that also the position of condensation of the radiative light L2 shifts in the X-direction. The center of the second optical fiber 2 is, therefore, preferably aligned at a position away from the origin in the X-direction. Accordingly, it is not preferable for this purpose to arrange, typically as illustrated in FIG. 5, a plurality of the second optical fibers 2, 2, . . . so as to surround the first optical fiber 1 at regular intervals to form a circle.

While FIG. 4A, FIG. 4B and FIG. 4C shows results of calculation when a spherical plano-convex lens is used as the lens 3, the position of condensation of the radiative light L2 will not vary if the focal length of the lens 3 is kept constant, even if the lens geometry varies among plano-convex, biconvex, spherical and aspherical, so long as the paraxial optics may be applied. Also any actual lens is assumed to cause only a small change.

Figure 6:
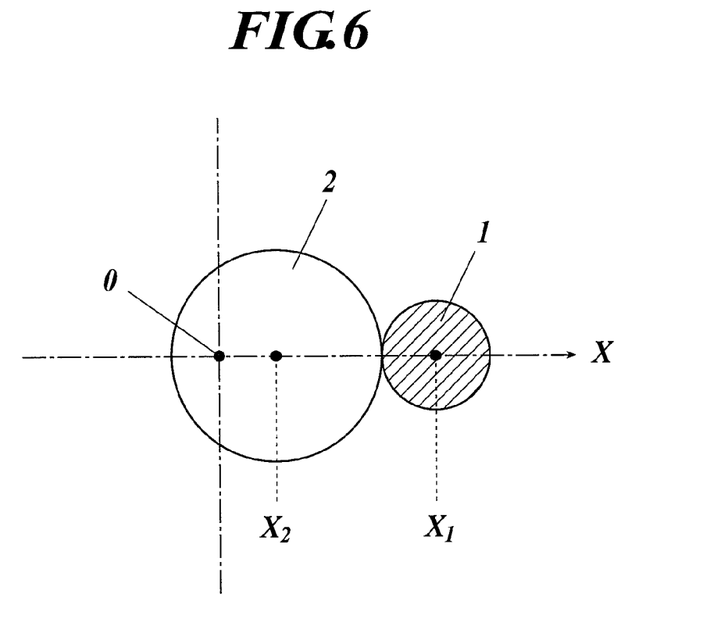
FIG. 6 This is a schematic front elevation illustrating an arrangement of the optical axis of the lens and the optical fibers of a probe according to one embodiment of the present invention.
Figure 7:
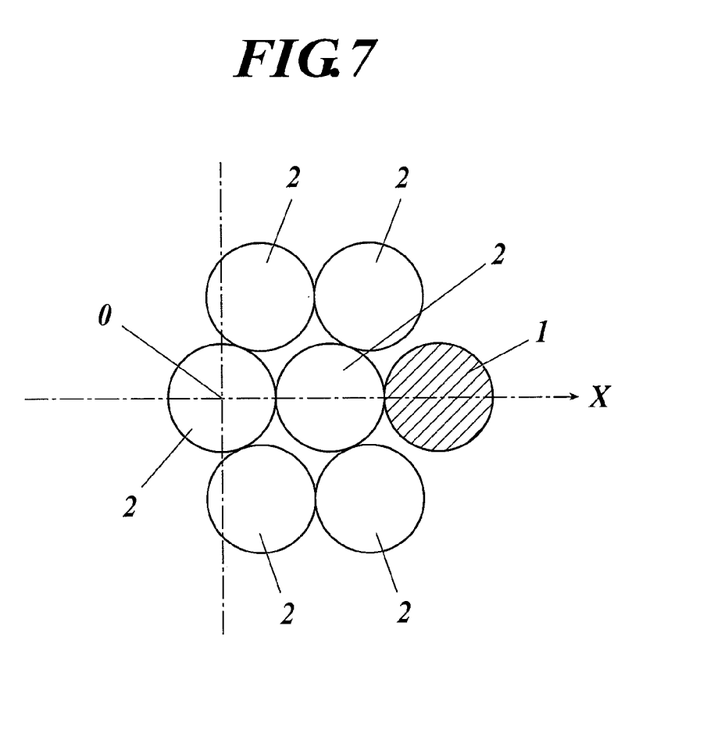
FIG. 7 This is a schematic front elevation illustrating an arrangement of the optical axis of the lens and the optical fibers of a probe according to another embodiment of the present invention.

FIGS. 6 and 7 show exemplary arrangements of the first optical fiber 1 and second optical fiber(s) 2 on the plane coordinate defined similarly as FIG. 4A, FIG. 4B and FIG. 4C. The X-axis represents a coordinate in the direction aligned with the center axis of the first optical fiber 1. Coordinate $X_1$ represents an X-coordinate of the first optical fiber 1. In FIG. 6, a single second optical fiber 2 is applied, wherein the center axis of the first optical fiber 1 is relatively shifted from the optical axis of the lens 3 and the center axis of the second optical fiber 2 is placed more closer to the optical axis of the lens 3 than to the center axis of the first optical fiber 1. In more detail, the center axis of the second optical fiber 2 is positioned between the center axis of the first optical fiber 1 and the optical axis of the lens 3. In furthermore detail, in view of making the position of condensation of the radiative light L2 and the center position of the second optical fiber 2 more closer, it is preferable to align the center axis of the second optical fiber 2 with the X-axis so that coordinate $X_2$ thereof satisfies $0<X_2<X_1$.

Since the minimum value of distance $(X_1-X_2)$ is limited by the clad diameters of the optical fibers 1 and 2, the diameters of the optical fibers 1 and 2 are respectively selected so that the optical fibers 1 and 2 may be arranged while satisfying the inequality above. The distance between the center axis of the first optical fiber 1 and the center axis of the second optical fiber 2 is preferably shorter than the diameter of the second optical fiber 2, so as to bring the both into close proximity.

For the case where a plurality of the second optical fibers 2 are applied as illustrated in FIG. 7, the light reception efficiency of the radiative light L2 by the second optical fibers 2 may be increased by arranging the plurality of second optical fibers 2, 2, . . . so that the input ends thereof are gathered at the center of condensation of the radiative light L2 condensed by the lens 3. One standard of crowdedness in this sort of gathered arrangement is given by making an average distance between the input ends of the plurality of second optical fibers 2, 2, . . . and the optical axis of the lens 3 shorter than an average distance between the input ends of the plurality of second optical fibers 2, 2, and the center $(X_1, 0)$ of the output end of the first optical fiber 1. More specifically, when the arrangement of the plurality of second optical fibers 2 is determined, such plurality of second optical fibers 2 are preferably more crowded around the optical axis of the lens 3 rather than around the center $(X_1, 0)$ of the output end. In other words, one effective standard is such that a total or average of the distance between the center of the input end of each second optical fiber 2 and the optical axis of the lens 3 is smaller than a total or average of the distance between the center of the input end of each second optical fiber 2 and the center $(X_1, 0)$ of the output end of the first optical fiber 1. Since the total number of the second optical fiber 2 is kept constant, the standard is kept unchanged irrespective of whether it is calculated based on the total or average.

Accordingly, for the case where a plurality of second optical fibers 2 are applied, a preferable arrangement of them is not such as that illustrated in FIG. 5 wherein the plurality of second optical fibers 2, 2, . . . are arranged so as to surround the first optical fiber at regular intervals but such as that illustrated in FIG. 7 wherein they are arranged one-sided on the origin 0 side of the first optical fiber 1.

Note that, the larger the number of the second optical fibers 2, the larger the amount of received light, whereas the smaller the number, the more advantageous the thinning, so that the number may be determined taking a desired level of light reception efficiency, the lens diameter and an allowable level of probe diameter into consideration.

Secondary effects obtainable by arranging the first optical fiber 1 so as to be shifted from the optical axis include an effect of increasing the light reception efficiency of the radiative light L2 and an effect of spatially separating, in a substantial manner, the radiative light L2 from the reflected light L3 from the lens 3, to thereby reduce input of the reflected light L3 from the lens 3 into the second optical fibers 2. As illustrated in FIG. 4A, FIG. 4B and FIG. 4C, by shifting the first optical fiber 1, the position of condensation of the reflected light L3 from the lens 3 characteristically shifts in the direction opposite to the first optical fiber 1. Accordingly, it becomes now possible to make the position of the center of condensation of the radiative light L2 and the position of the center of distribution of condensed reflected light from the lens 3 be different, and to greatly separate the position of condensation of the radiative light L2 and the position of condensation of reflected light L3 from the lens 3 in terms of space. Thus the light reception efficiency of the radiative light L2 may readily be increased without allowing the reflected light L3 from the lens 3 to enter the second optical fiber 2. In the embodiments illustrated in FIG. 4B and FIG. 4C, in a plane normal to the optical axis of the lens 3, the position of center of distribution of the reflected light L3 from the lens 3 resides on the opposite side of the center axis of the first optical fiber 1 while placing the optical axis of the lens 3 in between, and the center of condensation of the radiative light L2 resides more closer to the center axis of the first optical fiber 1 than to the optical axis of the lens 3. Accordingly, by arranging the center axis of the second optical fiber 2 more closer to the center axis of the first optical fiber 1 than to the optical axis of the lens 3, the reception efficiency of the radiative light L2 may be improved without allowing the reflected light L3 from the lens 3 to enter the second optical fiber 2.

The lens used in combination with the optical fibers 1 and 2 is characterized by condensation with a positive focal length. This sort of lens is roughly classified into three types.

That is, assuming now the radius of curvature of the lens surface opposed to the optical fibers 1 and 2 as R1 and the radius of curvature of the objective lens surface opposite thereto as R2, the three types are represented by (1) |R1|<|R2|, (2) |R1|>|R2|, and (3) |R1|=|R2|. These types are varied in the condensation characteristics of the reflected light from the lens as given by Referential Calculation Example 4 below, and are therefore varied in the effect of shifting the first optical fiber 1 relative to the optical axis of the lens.

Referential Calculation Example 4

Figure 8A:
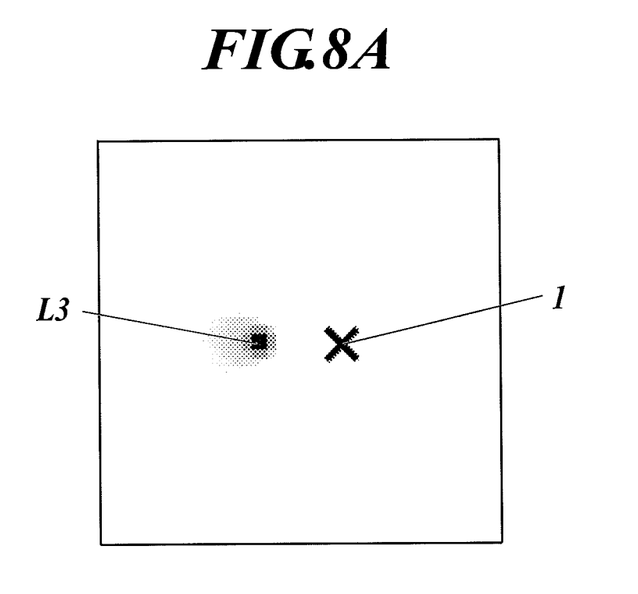
FIG. 8A This is a drawing illustrating a two-dimensional distribution of condensed reflected light after reflected on the surface of a semi-spherical lens having a spherical surface opposed to the first optical fiber.
Figure 8B:
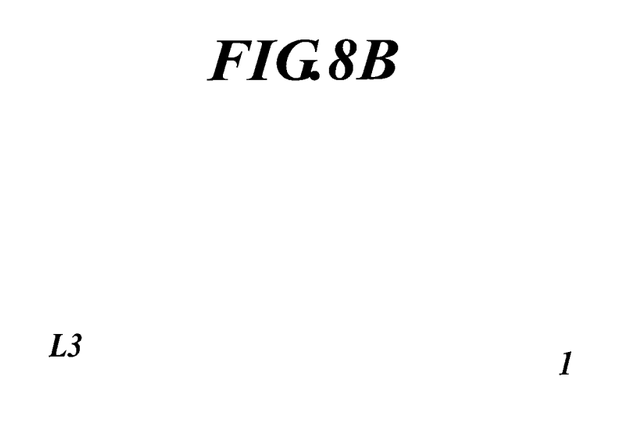
FIG. 8B This is a drawing illustrating a two-dimensional distribution of condensed reflected light after reflected on the surface of a biconvex lens.
Figure 8C:
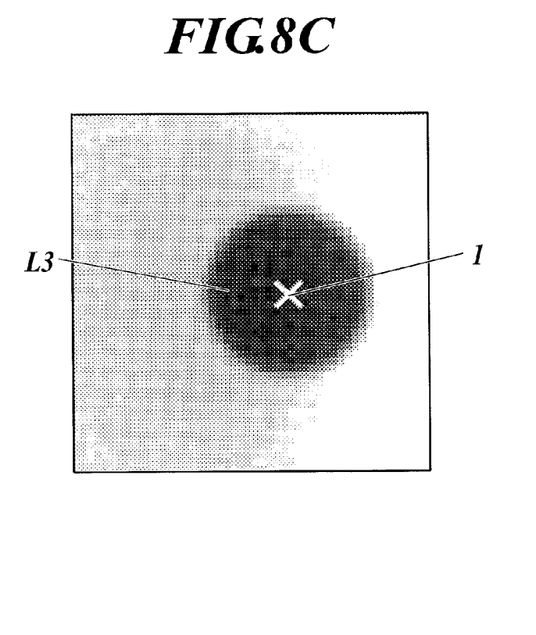
FIG. 8C This is a drawing illustrating a two-dimensional distribution of condensed reflected light after reflected on the surface of a semi-spherical lens having a flat surface opposed to the first optical fiber 1.

Distribution of Condensed Reflected Light from Individual Lenses with Different Geometries FIG. 8A, FIG. 8B and FIG. 8C are drawings illustrating two-dimensional distributions of condensed reflected light L3 after reflected on the surfaces of three types of lenses having different geometries. Marks "x" in the drawings indicate the center position of the first optical fiber 1. FIG. 8A corresponds to a semi-spherical lens having a spherical surface opposed to the first optical fiber 1. FIG. 8B corresponds to a biconvex lens. FIG. 8C corresponds to a semi-spherical lens having a flat surface opposed to the first optical fiber 1. Other detailed conditions for calculation are as follow.
(Conditions for Calculation)

Conditions for the first optical fiber are common for all, including a core diameter of 100 (μm), a NA of 0.23 and a shift from the optical axis of the lens of 0.2 (mm).

The lenses used in Calculation Examples illustrated in FIG. 8A and FIG. 8C have a spherical surface characterized by a radius of curvature of 0.83 (mm).

The lens used in Calculation Example illustrated in FIG. 8B has both surfaces characterized by a radius of curvature of 1.66 (mm).

All of the three lenses have an effective diameter of 1.66 (mm), a lens thickness of 0.83 (mm), and are characterized by $n_d=1.51633$ and $v_d=64.1$.

In common to all cases, the lenses are disposed so that the output light from the first optical fiber is collimated therethrough.

It is now understood that the lens applied to Calculation Example illustrated in FIG. 8A belongs to the lens type (1) described above, the lens applied to Calculation Example illustrated in FIG. 8B belongs to the lens type (3) and the lens applied to Calculation Example illustrated in FIG. 8C belongs to the lens type (2).

Also the semi-spherical lens applied to Referential Calculation Example 3, the results of which were illustrated in FIG. 4A, FIG. 4B and FIG. 4C, belongs to the lens type (1), most of which shift the position of condensation of the reflected light L3 from the lens in the direction opposite to the first optical fiber 1. Accordingly, again by satisfying $0<X_2<X_1$, a configuration suppressed in the amount of received reflected light L3 from the lens may be obtained. As for the lens type (2), most of which shift the position of condensation of the reflected light L3 from the lens in the same direction with the first optical fiber 1. They are, therefore, not suitable for the purpose of spatially separating the positions of condensation of the reflected light L3 from the lens and the radiative light L2 by shifting the first optical fiber 1. The lens type (3) has both features of the lens types (1) and (2). Judging from the above, for the purpose of shifting the first optical fiber 1 away from the optical axis of the lens so as to spatially separate the positions of condensation of the radiative light L2 and the reflected light L3 from the lens, preferable is the lens which belongs to the lens type (1). Preferable arrangement of the individual fibers corresponding thereto is as described above.

[Axis-Tilted Placement]

The secondary effect of separating the positions of condensation of the reflected light L3 from the lens and the radiative light L2 is also obtainable by tilting the lens per se, that is, by relatively tilting the center axis of the output end of the first optical fiber away from the optical axis of the lens. Such inclination may be given simply by placing the lens 3 in an tilted manner on the probe.

If the lens is not tilted with respect to the first optical fiber, the light output from the first optical fiber is reflected on the lens in a confronted manner, and is more likely to return back into the first optical fiber.

By tilting the lens relative to the optical axis of the first optical fiber at an angle not causative of the confronting reflection of light output from the first optical fiber, also the direction of returning back of the reflected light L3 will vary. In this way, the reflected light L3 returning back into the second optical fiber may be reduced.

Figure 9:
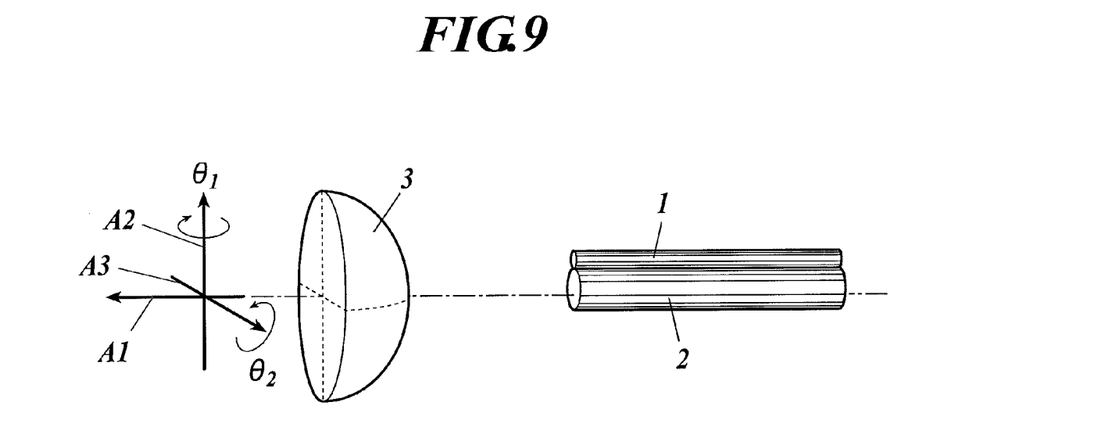
FIG. 9 This is a schematic drawing illustrating a three-dimensional arrangement for defining the direction of tilting of the lens.

Now, the direction of tilting of the lens is defined as illustrated in FIG. 9. Axis A1 represents the center axis of the output end of the first optical fiber 1 or an axis parallel thereto. Axis A2 crosses at right angles with axis A1 and is aligned with the center axis of the output end of the first optical fiber 1 and the center axis of the input end of the second optical fiber 2. Axis A3 crosses at right angles with axis A1 and axis A2. $\theta_1$ represents an angle around axis A2. $\theta_2$ represents an angle around axis A3.

Changes in the direction of travel of the reflected light L3 ascribable to the tilting of the lens 3 are independent of the lens geometry. For the purpose of separating the positions of condensation of the reflected light L3 from the lens and the radiative light L2, the lens is preferably tilted in the direction of $\theta_1$ so as to shift the position of condensation of the reflected light L3 from the lens in the direction of axis A3 around which angle $\theta_2$ is defined as illustrated in FIG. 9. In this case, an angle of tilting of 30° or smaller will not change the position of condensation of the radiative light L2. Therefore, the angle of tilting of the lens is preferably 30° or smaller, so long as the light output from the first optical fiber falls within the effective diameter of the lens.

By combining the shifting of the first optical fiber 1 and the tilting of the lens 3 described above, the shift of the position of condensation of the radiative light L2 away from the first optical fiber 1 and the shift of the radiative light L2 away from the reflected light L3 from the lens 3 may be controlled in an independent manner. Accordingly, it is now possible to pursuit so that the radiative light L2 is much more concentrated into the second optical fiber 2 and that the reflected light L3 is brought further away from the second optical fiber 2.

By virtue of the relative shift or/and relative inclination of the center axis of the output end of the first optical fiber 1 with respect to the optical axis of the lens 3 as described above, the reflected light from both surfaces of the condensing lens 3 is brought away from the center of the input end of the second optical fiber 2 disposed at a specific position with respective to the optical axis of the lens 3, and the radiative light from the living body condensed by the condensing lens 3 is condensed to the center of the input end of the second optical fiber 2. The radiative light from an object to be measured is now successfully incorporated into the second optical fiber 2 in a highly efficient manner while avoiding the reflected light from the condensing lens 3.

In an configuration using a single first optical fiber 1 and a single second optical fiber 2, the radiative light from a living body may be acquired in a highly efficient manner by making the core diameter of the second optical fiber 2 larger than the core diameter of the first optical fiber 1 as described above.

Also making the numerical aperture (NA) of the second optical fiber 2 larger than the numerical aperture (NA) of the first optical fiber 1 is effective for acquiring the radiative light from a living body in a highly efficient manner.

The illumination light guided through and output from the first optical fiber 1 or the radiative light preferably has the wavelength within the range from 340 (nm) to 750 (nm) for better practicability, in view of implementing the measurement without using ultraviolet radiation or infrared radiation which possibly damages the living body.

In addition, the illumination light guided through and output from the first optical fiber 1 or the radiative light, preferably has the wavelength within the range from 300 (nm) to 1000 (nm) for better practicability, in view of avoiding damage on genes in the living body and in view of implementing the measurement within the range of sensitivity of ordinary sensors for receiving the radiative light from a living body.

While the embodiments described above dealt with the case where the optical fiber is used for illuminating the excitation light to a site of observation and for receiving fluorescence ascribable to the excitation light, the optical fiber may receive scattered light or Raman scattered light ascribable to the illumination light. Also these cases are applicable to diagnosis of status of disease including denaturation of biological tissues and cancer, and can yield the effects of the present invention.

INDUSTRIAL APPLICABILITY

The probe of the present invention is applicable to optical measurement of biological tissues, for the purpose of understanding state of biological tissues including state of lesion.

EXPLANATION OF REFERENCE NUMERALS 1 first optical fiber
2 second optical fiber
3 condensing lens
4 surface of biological tissue
10 probe
L1 excitation light
L2 radiative light
L3 reflected light from lens surface

The invention claimed is:

1. A probe having an optical system which illuminates an illumination light to a site of measurement of a biological tissue and receives a radiative light radiated from the site of measurement, and configured so as to measure the radiative light, the probe comprising:
 a first optical fiber which configures an illumination light guide through which the illumination light is guided and a second optical fiber which configures a receiving light guide through which the radiative light is acquired, the first optical fiber and the second optical fiber being independent from each other;
 a condensing lens which receives the illumination light output from the first optical fiber and outputs the received illumination light towards the site of measurement and which receives the radiative light radiated from the site of measurement and condenses the received radiative light towards the second optical fiber,
 wherein the first optical fiber is aligned so as to shift a center axis of an output end of the first optical fiber away from an optical axis of the condensing lens or/and relatively inclined from the optical axis of the condensing lens, and when compared with a configuration without shift and inclination, a reflected light from a surface of the condensing lens is brought away from a center axis of an input end of the second optical fiber and the radiative light condensed by the condensing lens is brought closer to the center axis of the input end of the second optical fiber, and
 wherein, in a plane normal to the optical axis of the condensing lens, a center of distribution of the reflected light from the condensing lens is positioned opposite to the center axis of the output end of the first optical fiber while placing the optical axis of the condensing lens in between, and the center of condensation of the radiative light is positioned closer to the center of the output end of the first optical fiber than to the optical axis of the condensing lens.

2. The probe of claim 1, wherein the center axis of the output end of the first optical fiber is relatively shifted from the optical axis of the condensing lens, and the center axis of the input end of the second optical fiber is positioned closer to the optical axis of the condensing lens than to the center axis of the output end of the first optical fiber.

3. The probe of claim 2, wherein the center axis of the input end of the second optical fiber is positioned between the center axis of the output end of the first optical fiber and the optical axis of the condensing lens.

4. The probe of claim 1, wherein the numerical aperture of the second optical fiber is larger than the numerical aperture of the first optical fiber.

5. The probe of claim 1, comprising one or a plurality of the first optical fibers and one or a plurality of the second optical fibers, wherein the total core area of the second optical fiber(s) is larger than the total core area of the first optical fiber(s).

6. The probe of claim 1, comprising a plurality of the second optical fibers, wherein the input ends of the plurality of second optical fibers are arranged to be gathered at the center of condensation of the radiative light condensed by the condensing lens.

7. The probe of claim 6, wherein an average distance from the input ends of the plurality of second optical fibers to the optical axis of the condensing lens is shorter than an average distance from the input ends of the plurality of second optical fibers to the center axis of the output end of the first optical fiber.

8. The probe of claim 1, wherein the illumination light or the radiative light has a wavelength of 300 nm to 1100 nm.

9. The probe of claim 1, wherein the illumination light or the radiative light has a wavelength of 340 nm to 750 nm.

10. The probe of claim 1, wherein a distance between the center axis of the first optical fiber and the center axis of the second optical fiber is shorter than a diameter of the second optical fiber.

11. The probe of claim 1, wherein when a radius of curvature of the lens surface of the condensing lens opposed to the first optical fiber and the second optical fiber is R1 and a radius of curvature of the objective lens surface of the condensing lens is R2, a relation between R1 and R2 is: $|R1|<|R2|$.

* * * * *